US012643921B2

(12) United States Patent
Collins et al.

(10) Patent No.: US 12,643,921 B2
(45) Date of Patent: Jun. 2, 2026

(54) PROCESSES FOR PREPARING C-4 SUGARS AND KETOSE SUGARS

(71) Applicant: Archer Daniels Midland Company, Decatur, IL (US)

(72) Inventors: William J. Collins, Mt. Zion, IL (US); Josh Terrian, Mt. Zion, IL (US); James Brazdil, Leland, NC (US); Kevin Martin, Mt. Zion, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 831 days.

(21) Appl. No.: 17/998,295

(22) PCT Filed: Apr. 30, 2021

(86) PCT No.: PCT/US2021/030350

§ 371 (c)(1),
(2) Date: Nov. 9, 2022

(87) PCT Pub. No.: WO2021/231111

PCT Pub. Date: Nov. 18, 2021

(65) Prior Publication Data

US 2023/0242563 A1 Aug. 3, 2023

Related U.S. Application Data

(60) Provisional application No. 63/023,765, filed on May 12, 2020.

(51) Int. Cl.

| | |
|---|---|
| ***C07H 3/02*** | (2006.01) |
| ***B01J 31/18*** | (2006.01) |
| ***B01J 35/51*** | (2024.01) |
| ***C07H 1/00*** | (2006.01) |

(52) U.S. Cl.

CPC ............ *C07H 3/02* (2013.01); *B01J 31/1815* (2013.01); *B01J 35/51* (2024.01); *C07H 1/00* (2013.01); *B01J 2231/342* (2013.01); *B01J 2531/0216* (2013.01); *B01J 2531/26* (2013.01)

(58) Field of Classification Search

CPC ........................................................ C07H 3/02
USPC .......................................................... 536/124
See application file for complete search history.

(56) References Cited

U.S. PATENT DOCUMENTS

| | | | | |
|---|---|---|---|---|
| 7,094,932 | B2 * | 8/2006 | Majerski | C07C 45/673 568/465 |
| 12,421,184 | B2 * | 9/2025 | Collins | B01J 21/08 |
| 2004/0022912 | A1 | 2/2004 | Majerski et al. | |
| 2015/0307786 | A1 | 10/2015 | Dayton et al. | |
| 2017/0191095 | A1 * | 7/2017 | Marliere | C12Y 203/03015 |

FOREIGN PATENT DOCUMENTS

WO 2018104508 6/2018

OTHER PUBLICATIONS

Murillo, Beatriz et, al., "Chemocatalysis of Sugars to Produce Lactic Acid Derivatives on Zeolitic Imidazolate Frameworks" Journal of Catalysis 2016. vol. 334, pp. 60-67 (online published: Dec. 17, 2015) abstract; pp. 61-62.

* cited by examiner

*Primary Examiner* — Traviss C McIntosh, III
(74) *Attorney, Agent, or Firm* — Andrew F. Nilles

(57) ABSTRACT

Various processes for preparing $C_4$ aldoses and/or ketones thereof are described. Various processes are described for preparing $C_4$ aldoses and/or ketones thereof from feed compositions comprising glycolaldehyde. Also, various processes for preparing useful downstream products and intermediates, such as erythritol and erythronic acid, from the $C_4$ aldoses and/or ketones thereof are described.

17 Claims, No Drawings

PROCESSES FOR PREPARING C-4 SUGARS AND KETOSE SUGARS

CROSS-REFERENCE TO RELATED APPLICATIONS

This application is a national stage entry of International Application No. PCT/US21/30350, filed Apr. 30, 2021, which itself claims priority to U.S. Provisional Patent Application No. 63/023,765, filed May 12, 2020, the contents of each are incorporated herein by reference.

FIELD OF THE INVENTION

The present invention relates to various processes for preparing $C_4$ aldoses and/or ketones thereof. The present invention further relates to various processes for preparing useful downstream products and intermediates, such as erythritol and erythronic acid, from the $C_4$ aldoses and/or ketones thereof.

BACKGROUND

Pyrolysis of glucose (dextrose) and other carbohydrate feedstocks produces a reaction product that contains a variety of aldehyde compounds such as glyoxal, pyruvaldehyde, acetol, ethylene glycol, and glycolaldehyde. Of these compounds, glycolaldehyde is generally considered the most valuable (e.g., see WO 88/00935 A1). Glycolaldehyde can be used as-is, such as in the production of liquid smoke (e.g., as described in U.S. Pat. No. 6,074,679), or as a precursor reagent in the synthesis of methionine (e.g., see U.S. Pat. No. 10,189,778). However, there remains a need for additional reactions and effective processes that can utilize glycolaldehyde as a starting material to more fully capture the value of this compound.

BRIEF SUMMARY

Various aspects of the present invention are directed to processes for preparing $C_4$ aldoses and/or ketones thereof. In some embodiments, the processes comprise contacting a feed composition comprising glycolaldehyde with a catalyst comprising an imidazolate framework (e.g., zeolitic imadazolate framework (ZIF) or boron imidazolate framework (BIF)) in a reaction zone to condense at least a portion of the glycolaldehyde to the $C_4$ aldose and/or ketone thereof.

Other aspects are directed to processes for generating a feed composition with improved yields of glycolaldehyde through a catalyzed pyrolysis of carbohydrates and then preparing $C_4$ aldoses and/or ketones thereof from the feed composition thus generated. In some embodiments, the preparation of the $C_4$ aldoses and/or ketones thereof comprises contacting this feed composition with a catalyst comprising an imidazolate framework (e.g., zeolitic imadazolate framework (ZIF) or boron imidazolate framework (BIF)) in a reaction zone to condense at least a portion of the glycolaldehyde in the feed composition demonstrating improved yields of glycolaldehyde, to the $C_4$ aldose and/or ketone thereof.

Further aspects are directed to processes for preparing erythritol and/or threitol. In various embodiments, the processes comprise preparing erythrose and/or threose according to processes as described herein; and hydrogenating at least a portion of the erythrose and/or threose to form the erythritol and/or threitol.

Still other aspects are directed to processes for preparing erythronic acid, threonic acid, and/or a salt thereof. In some embodiments, the processes comprise preparing erythrose and/or threose according to processes as described herein; and oxidizing at least a portion of the erythrose and/or threose to form the erythronic acid, threonic acid, and/or salt thereof.

Still other aspects are directed to processes for preparing for preparing a downstream product. These processes comprise preparing a $C_4$ aldose and/or ketone thereof according to processes as described herein; converting the $C_4$ aldose and/or ketone thereof to a downstream product or a precursor thereof, wherein the downstream product is a compound selected from the group consisting of glyceraldehyde; methyl vinyl glycolate; 2-hydroxy-4-methoxybutanoate; 2-hydroxy-4-methoxybutanoic acid; 1,4-butanediol; α-hydroxy-γ-butyrolactone, methionine, and analogues thereof.

Other objects and features will be in part apparent and in part pointed out hereinafter.

DETAILED DESCRIPTION

The present invention relates to various processes for preparing $C_4$ aldoses and/or ketones thereof. The present invention further relates to various processes for preparing useful downstream products and intermediates, such as erythritol and erythronic acid, from the $C_4$ aldoses and/or ketones thereof (i.e., $C_4$ sugars and ketose sugars).

Certain embodiments of processes of the present invention have been found to selectively produce $C_4$ sugars and their corresponding ketoses such as threose, erythrose and erythrulose from feed compositions comprising glycolaldehyde at enhanced conversion rates. In particular, for these embodiments, it has been discovered that glycolaldehyde can be condensed to one or more $C_4$ aldoses and/or ketones in high yields and/or selectivities by employing a catalyst comprising an imidazolate framework (e.g., zeolitic imidazolate framework (ZIF) or boron imidazolate framework (BIF)). It has also been discovered that these catalysts can provide for reduced reaction times, which can advantageously increase catalyst productivity and process economics. Accordingly, various processes for preparing $C_4$ aldoses and/or ketones thereof comprise contacting a feed composition comprising glycolaldehyde with a catalyst comprising an imidazolate framework in a reaction zone to condense at least a portion of the glycolaldehyde to the $C_4$ aldose and/or ketone thereof.

Condensation Catalysts

As noted, the condensation reaction in preferred embodiments of the processes described herein are conducted in the presence of a catalyst comprising an imidazolate framework. Imidazolate frameworks comprise one or more metals and/or metalloids connected by imidazolate/imidazolate-type linking groups. For example, the one or more metals and/or metalloids can include zinc, cobalt, copper, iron, lithium, boron and combinations thereof. In various embodiments, the imidazolate framework comprises zinc. In some embodiments, the imidazolate framework comprises boron. The linking group can be, for instance, imidazolate (IM), 2-methylimidazolate (MIM), 2-ethylimidazolate (EIM), and benzimidazolate (BIM).

In various embodiments, the catalyst comprises an imidazolate framework comprising a zeolitic imidazolate framework (ZIF) or a boron imidazolate framework (BIF). In various embodiments, the catalyst comprises a ZIF. In some embodiments, the catalyst comprises a BIF. In certain embodiments, the catalyst comprises an imidazolate framework selected from the group consisting of ZIF-4, ZIF-8, ZIF-14, BIF-2Li, BIF-2Cu, BIF-5, and combinations thereof. In particular embodiments, the catalyst comprises an imidazolate framework comprising a ZIF-4 ($ZnIM_2$)). In some embodiments, the catalyst consists essentially of ZIF-4 (e.g., 95% or more, or 99% or more by weight of the total catalyst weight). In certain embodiments, the catalyst consists of ZIF-4.

The imidazolate framework can be prepared from precursors comprising imidazole and/or an imidazole-type compounds (e.g., 2-methylimidazole, 2-ethylimidazole, and benzimidazole in combination with one or more salts (e.g., metal nitrate). In various embodiments, the imidazolate framework is prepared from precursors comprising imidazole and zinc nitrate hexahydrate.

In various embodiments, the imidazolate framework and/or the catalyst is essentially free of tin, zirconia, and/or silica (e.g., containing 1% or less, though preferably 0.1% or less, or even 0.01% or less by weight of the total catalyst weight). In various embodiments, the imidazolate framework and/or the catalyst is free of tin, zirconia, and/or silica. In some embodiments, the imidazolate framework and/or the catalyst is free or essentially free of tin. In further embodiments, the imidazolate framework and/or the catalyst is free or essentially free of zirconia. In certain embodiments, the imidazolate framework and/or the catalyst is free or essentially free of silica.

Further, in some embodiments, the reaction zone is essentially free of zeolite catalysts including pentasil zeolites such as ZSM-5 and ZSM-11 (e.g., containing 1% or less, though preferably 0.1% or less, or even 0.01% or less by weight of the total catalyst weight). In certain embodiments, the reaction zone is free of zeolite catalysts including pentasil zeolites.

Feed Materials

As noted, the feed composition used for preparing the $C_4$ aldoses and/or ketones thereof in all embodiments comprises glycolaldehyde. For example, the feed composition can comprise a glycolaldehyde concentration of about 1 wt. % or greater, about 5 wt. % or greater, about 10 wt. % or greater, about 20 wt. % or greater, about 30 wt. % or greater, about 40 wt. % or greater, about 50 wt. % or greater, about 60 wt. % or greater, or about 70 wt. % or greater. In some embodiments, the feed composition comprises a glycolaldehyde concentration of from about 1 wt. % to about 70 wt. %, from about 1 wt. % to about 50 wt. %, from about 1 wt. % to about 25 wt. %, or from about 1 wt. % to about 10 wt. %. In various embodiments, the feed composition further comprises water (e.g., the feed composition is an aqueous solution comprising glycolaldehyde).

The glycolaldehyde of the feed composition can be obtained from a pyrolysis process where carbohydrates such as glucose are converted to shorter chain compounds. Various examples of such processes are known and could be employed, see, e.g., (U.S. Pat. Nos. 5,252,188; 5,397,582; and 7,094,932; as well as Schandel et al., *ChemSusChem* 2020, 13, 688., with a preferred process, however, being as described in commonly-assigned U.S. Ser. No. 63/023,763, filed concurrently herewith for "Processes for the Pyrolysis of Carbohydrates" and incorporated by reference herein, whereby improved yields of glycolaldehyde are provided from carbohydrate pyrolysis from which $C_4$ aldoses and/or ketones thereof may be prepared by a condensation reaction generally, but in particular and especially by a condensation reaction employing a catalyst comprising an imidazolate framework such as described and exemplified herein. Accordingly, in some embodiments, at least a portion of the glycolaldehyde used for preparing the $C_4$ aldoses and/or ketones is obtained from pyrolysis of a carbohydrate such a glucose. In certain embodiments, the feed composition contains other components. For example, compounds such as pyruvaldehyde, formaldehyde, acetol, and glyoxal can be produced by the pyrolysis of a carbohydrate. Accordingly, in various embodiments, the feed composition can further comprise at least one compound selected from the group consisting of pyruvaldehyde, formaldehyde, acetol, glyoxal, and combinations thereof.

Carbohydrates can be obtained from various conventional biorenewable sources such as corn grain (maize), wheat, potato, cassava and rice, as well as alternative sources such as energy crops, plant biomass, agricultural wastes, forestry residues, sugar processing residues, and plant-derived household wastes. In various embodiments, the carbohydrate is obtained from a grain crop (e.g., corn, wheat, soybean, rice, barley, rye, millet, sorghum, etc.). More generally, biorenewable sources that can be used include any renewable organic matter that includes a source of carbohydrates such as, for example, switch grass, *miscanthus*, trees (hardwood and softwood), vegetation, and crop residues (e.g., bagasse and corn stover). Other sources include, for example, waste materials (e.g., spent paper, green waste, municipal waste, etc.). Carbohydrates can be isolated from biorenewable materials using known methods.

Carbohydrates obtained from these sources can include various monosaccharides, disaccharides, oligosaccharides, and polysaccharides (e.g., a $C_4$-$C_{24}$ saccharide). In certain embodiments, the carbohydrate comprises at least one saccharide selected from the group consisting of a monosaccharide, a disaccharide, an oligosaccharide, and combinations thereof. In various embodiments, the carbohydrate comprises a monosaccharide. Carbohydrates can also include a cellulose.

In some embodiments, the carbohydrate includes a sugar having at least four carbon atoms. For example, sugars include various aldoses. Aldoses, as referred to herein, include various compounds possessing an aldehyde and hydroxyl groups, which can be represented by formula (I):

$$HOCH_2(HCOH)_wCHO \quad (I)$$

where w can be, for example, an integer from 2 to 10 or, in some embodiments, from 2 to 5. In various embodiments, the carbohydrate comprises at least one $C_4$-$C_7$ aldose. In some embodiments, the carbohydrate comprises at least one sugar selected from the group consisting of tetrose, pentose, hexose, heptose, and mixtures thereof. Specific $C_4$-$C_7$ aldoses include, for example, threose, erythrose, xylose, ribose, arabinose, glucose, galactose, mannose, glucoheptose, L-glycero-D-manno-heptose, and mixtures thereof. In various embodiments, the carbohydrate comprises a hexose such as glucose (dextrose). In some embodiments, the carbohydrate comprises a pentose such as xylose, ribose, and/or arabinose. The term "aldoses" and any specific aldose mentioned herein and as defined by formula (I) also include cyclic forms (hemiacetal forms) of these compounds.

In some embodiments, the carbohydrate includes a ketose sugar having at least four carbon atoms. In various embodiments, the carbohydrate comprises at least one ketose sugar selected from the group consisting of a ketotetrose, ketopentose, ketohexose, ketoheptose, and mixtures thereof. In certain embodiments, the carbohydrate comprises fructose.

Process Features

The condensation reaction for preparing $C_4$ aldoses and/or ketones thereof from such feeds, especially in relation to the use for such purposes of a catalyst comprising an imidazolate framework, can be conducted at a temperature of about 100° C. or less, about 95° C. or less, about 90° C. or less. In various embodiments, the reaction is conducted at a temperature of about 0° C. or greater, about 25° C. or greater, about 50° C. or greater, or about 80° C. or greater. In some embodiments, the reaction is conducted at a temperature of from about 25° C. to about 100° C., from about 25° C. to about 90° C., from about 50° C. to about 100° C., from about 50° C. to about 90° C., from about 80° C. to about 100° C., or form about 80° C. to about 90° C.

Advantageously, various processes of the present invention do not require caustic conditions in the reaction zone. Surprisingly, it has been found that a catalyst comprising an imidazolate framework as described herein can be effective under neutral and acidic conditions. Without being bound by theory, caustic conditions are believed to encourage intermolecular reactions such as polymerization and dimerization, as shown below for glycolaldehyde:

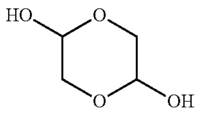

Similarly, formaldehyde (another potential component of the feed composition) can form trimeric molecules and polymers as shown below.

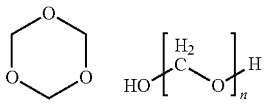

Surprisingly, it has been found that a catalyst comprising an imidazolate framework can be effective under neutral or acidic conditions.

Under acidic conditions, these dimerized/trimerized/polymerized molecules are believed to more likely to exist in their single-molecule forms. Processes capable of operating under neutral or acidic conditions can beneficially avoid formation of these compounds and avoid the energy input required to revert these aldehydes to their original forms. Accordingly, in various embodiments, the reaction is conducted at a pH of about 7 or less, about 6 or less, or about 5 or less. In certain embodiments, the reaction is conducted at a pH that is approximately neutral. In certain embodiments, the reaction is conducted free or essentially free of added base.

Further, various processes of the present invention do not require the addition of chemical additives such as organic solvents for the condensation reaction. Surprisingly, it has been found that the catalyst comprising an imidazolate framework can be effective without organic solvents. Accordingly, in various embodiments, the feed composition and/or reaction zone for carrying out the condensation reaction is free or essentially free of an organic solvent. In some embodiments, the feed composition and/or reaction zone is free of an alcohol solvent. In certain embodiments, the feed composition and/reaction zone is free or essentially free of methanol and/or ethanol. Unless stated otherwise herein, "essentially free" refers to a concentration that is 1% or less, though preferably the concentration can be 0.1% or less, or even 0.01% or less by weight of the chemical components fed to the reaction zone not including the catalyst (e.g., the feed composition).

Various processes can provide for enhanced conversion of glycolaldehyde in the condensing step. In some embodiments, the conversion of glycolaldehyde is about 90% or greater, about 95% or greater, or about 99% or greater. Various processes of the present invention can provide for enhanced conversion of glycolaldehyde at reduced reaction times in the condensing to form the desired $C_4$ aldoses and/or ketones. For example, in certain embodiments, the conversion of glycolaldehyde that is 90% or greater, 91% or greater, 92% or greater, 93% or greater, 94% or greater, 95% or greater, 96% or greater, 97% or greater, 98% or greater, or 99% or greater is achieved in a reaction time of about 10 hours or less, 8 hours or less, about 6 hours or less, or about 4 hours or less.

The processes of the present invention are thus effective for preparing a $C_4$ aldose and/or ketone thereof. In various embodiments, the $C_4$ aldose and/or ketone thereof comprises at least one compound selected from the group consisting of erythrose, threose, erythrulose, and combinations thereof. In certain embodiments, the $C_4$ aldose and/or ketone thereof comprises erythrose. In some embodiments, the $C_4$ aldose and/or ketone thereof comprises threose. In certain embodiments, the $C_4$ aldose and/or ketone thereof comprises erythrulose.

Various processes of the present invention can provide enhanced selectivity for erythrose, threose, erythrulose, and/or combinations thereof. In some embodiments, the selectivity of the condensing reaction for erythrose, threose, erythrulose, and/or combinations thereof is about 80% or greater, about 85% or greater, about 90% or greater, about 93% or greater, about 95% or greater, about 97% or greater, or about 99% or greater. In certain embodiments, the selectivity of the reaction for the combination of erythrose, threose, and erythrulose is about 80% or greater, about 85% or greater, about 90% or greater, about 93% or greater, about 95% or greater, about 97% or greater, or about 99% or greater.

In various embodiments, the selectivity of the condensing reaction for erythrose is about 10% or greater, about 15% or greater, about 20% or greater, about 25% or greater, about 30% or greater, about 35% or greater, about 40% or greater, or about 50% or greater (e.g., from about 10% to about 50%, from about 10% to about 40, or from about 15% to about 30%).

In some embodiments, the selectivity of the condensing reaction for threose is about 10% or greater, about 15% or greater, about 20% or greater, about 25% or greater, about 30% or greater, about 35% or greater, about 40% or greater, or about 50% or greater (e.g., from about 10% to about 50%, from about 10% to about 40, or from about 15% to about 30%).

In certain embodiments, the selectivity of the condensing reaction for erythrulose is about 10% or greater, about 15% or greater, about 20% or greater, about 25% or greater, about 30% or greater, about 35% or greater, about 40% or greater, or about 50% or greater (e.g., from about 10% to about 50%, from about 10% to about 40, or from about 15% to about 30%).

Pyrolysis of Carbohydrates

As noted, at least a portion of the glycolaldehyde in the feed composition can be obtained from a carbohydrate pyrolysis process. In some embodiments, the processes of the present invention further comprise pyrolyzing a carbohydrate to form glycolaldehyde. In various embodiments, the pyrolysis process comprises pyrolyzing a carbohydrate having at least four carbon atoms in the presence of water and a pyrolysis catalyst in a pyrolysis reaction zone to form a reaction product comprising glycolaldehyde, for example, as contemplated in the commonly-assigned, concurrently-filed U.S. Ser. No. 63/023,763 incorporated by reference above. In various embodiments, the pyrolysis catalyst comprises a metal oxide on a catalyst support.

In general, processes for the pyrolysis of carbohydrate can be used to prepare compounds such as glycolaldehyde, methylglyoxal/pyruvaldehyde, acetol/hydroxyacetone, and formaldehyde. "Carbohydrate(s)" and/or "carbohydrate feed" as used herein will be understood as including biomass feedstocks in any form which contain or which provide carbohydrates, especially carbohydrates having four or more carbon atoms, from which glycolaldehyde may be obtained under pyrolytic conditions.

Various pyrolysis processes have been found to produce glycolaldehyde in enhanced yields. Prior attempts to increase yields of glycolaldehyde have primarily focused on modifying feed concentrations and reactor conditions while the bed material and/or pyrolysis catalyst has remained largely unchanged. However, it has been surprisingly discovered that certain pyrolysis catalysts (typically, though not necessarily, in the form of a fluidizable, supported catalyst combined with the conventional bed material or materials supplied for heat transfer to the carbohydrate feed) can greatly affect the pyrolysis reaction and overcome the problems encountered by prior processes.

More particularly, as related in the commonly-assigned, concurrently-filed application referenced above, it has been discovered that certain metal oxides are particularly effective in improving the yield of desirable products such as glycolaldehyde from the pyrolysis of carbohydrates, especially sugars such as glucose. The pyrolysis processes described therein incorporating these catalysts can advantageously provide for improved process economics and reduced amounts of undesired products that may require separation from the product mixture and special handling and disposal. For example, the pyrolysis processes using these catalysts may make more productive use of process inputs (e.g., by requiring less energy), produce reduced amounts of undesired byproducts, and/or produce less char in producing a given quantity of glycolaldehyde and other desired products, than would be experienced in the absence of the catalysts. Further, various pyrolysis processes described herein have the advantage of providing for stable product yields over extended operation and/or at high reactor throughputs.

Accordingly, preferred methods for forming the $C_4$ aldoses and/or ketones will make use of improved pyrolysis processes for preparing glycolaldehyde. For example, some embodiments further comprise preparing glycolaldehyde comprising: feeding a feed composition comprising a carbohydrate having at least four carbon atoms to a pyrolysis reaction zone; and pyrolyzing the carbohydrate in the presence of water and a catalyst in the pyrolysis reaction zone to form a reaction product comprising glycolaldehyde, wherein the catalyst comprises a metal oxide on a catalyst support.

In general, the pyrolysis feed composition comprises a carbohydrate having at least four carbon atoms. For example, in some embodiments, the pyrolysis feed composition comprises a carbohydrate comprising a $C_4$-$C_{24}$ carbohydrate. Such carbohydrates can be obtained from various conventional biorenewable sources as described herein. Other sources include, for example, waste materials (e.g., spent paper, green waste, municipal waste, etc.). Carbohydrates can be isolated from biorenewable materials using known methods. The carbohydrates may be provided in the form of a carbohydrate solution (e.g., an aqueous glucose solution) or as comminuted solids of such biomasses.

Carbohydrates obtained from these sources can include various monosaccharides, disaccharides, oligosaccharides, and polysaccharides as described herein. Carbohydrates can also include a cellulose. In some embodiments, the carbohydrate includes a sugar having at least four carbon atoms. For example, sugars include various aldoses as described herein.

In some embodiments, the carbohydrate includes a ketose sugar having at least four carbon atoms. In various embodiments, the carbohydrate comprises at least one ketose sugar selected from the group consisting of a ketotetrose, ketopentose, ketohexose, ketoheptose, and mixtures thereof. In certain embodiments, the carbohydrate comprises fructose.

The pyrolysis feed composition can have a carbohydrate concentration that is about 1 wt. % or greater, about 5 wt. % or greater, about 10 wt. % or greater, about 15 wt. % or greater, or about 20 wt. % or greater. For example, in various embodiments, the feed composition has a carbohydrate concentration that is from about 1 wt. % to about 50 wt. %, from about 1 wt. % to about 30 wt. %, from about 1 wt. % to about 25 wt. %, from about 5 wt. % to about 50 wt. %, from about 5 wt. % to about 30 wt. %, from about 5 wt. % to about 25 wt. %, from about 10 wt. % to about 50 wt. %, from about 10 wt. % to about 30 wt. %, from about 10 wt. % to about 25 wt. %, from about 15 wt. % to about 50 wt. %, from about 15 wt. % to about 30 wt. %, from about 15 wt. % to about 25 wt. %, from about 20 wt. % to about 50 wt. %, from about 20 wt. % to about 30 wt. %, or from about 20 wt. % to about 25 wt. %.

As noted, a preferred pyrolysis process used to generate the glycolaldehyde from which the $C_4$ aldoses and/or ketones may be obtained by condensation will be one that is conducted in the presence of a catalyst comprising a metal oxide on a catalyst support. In various embodiments, the metal oxide comprises a transition metal oxide. For example, the metal oxide comprises an oxide of a group 4, 5, 6, 7, 8, 9, 10, or 11 metal or a mixture thereof. In some embodiments, the metal oxide comprises an oxide of a group 4, 5, or 6 metal or a mixture thereof. In certain embodiments, metal oxide comprises an oxide of titanium, molybdenum, tungsten, vanadium, or a mixture thereof. In particular embodiments, the metal oxide comprises an oxide of a molybdenum, tungsten, vanadium, or a mixture thereof. In certain embodiments, the metal oxide comprises an oxide of tungsten, molybdenum, or a mixture thereof. Preferred metal oxides typically include those that preferentially catalyze retro-aldol chemistry.

Oxides of molybdenum and tungsten have been found to be particularly effective for the pyrolysis catalysts. Accordingly, in various embodiments the metal oxide comprises tungsten oxide. For instance, the tungsten oxide can comprise tungsten (IV) oxide and/or tungsten (V) oxide. In some embodiments, the metal oxide comprises molybdenum oxide.

In some embodiments, tungsten oxide and/or molybdenum oxide constitute a significant portion of the metal oxide on the catalyst support. For example, in some embodiments, tungsten oxide and/or molybdenum oxide constitutes about 1 wt. % or greater, about 2 wt. % or greater, about 3 wt. % or greater, about 4 wt. % or greater, about 5 wt. % or greater, about 10 wt. % or greater, about 15 wt. % or greater, about 20 wt. % or greater, about 25 wt. % or greater, about 30 wt.

% or greater, about 35 wt. % or greater, about 40 wt. % or greater, about 45 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater of the metal oxide on the catalyst support. In various embodiments, tungsten oxide and/or molybdenum oxide constitutes from about 1 wt. % to about 99 wt. %, from about 2 wt. % to about 99 wt. %, from about 3 wt. % to about 99 wt. %, from about 4 wt. % to about 99 wt. %, from about 5 wt. % to about 99 wt. %, from about 10 wt. % to about 99 wt. %, from about 15 wt. % to about 99 wt. %, from about 20 wt. % to about 99 wt. %, from about 25 wt. % to about 99 wt. %, from about 30 wt. % to about 99 wt. %, from about 35 wt. % to about 99 wt. %, from about 40 wt. % to about 99 wt. %, from about 45 wt. % to about 99 wt. %, from about 50 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 95 wt. % to about 99 wt. %, from about 1 wt. % to about 95 wt. %, from about 2 wt. % to about 95 wt. %, from about 3 wt. % to about 95 wt. %, from about 4 wt. % to about 95 wt. %, from about 5 wt. % to about 95 wt. %, from about 10 wt. % to about 95 wt. %, from about 15 wt. % to about 95 wt. %, from about 20 wt. % to about 95 wt. %, from about 25 wt. % to about 95 wt. %, from about 30 wt. % to about 95 wt. %, from about 35 wt. % to about 95 wt. %, from about 40 wt. % to about 95 wt. %, from about 45 wt. % to about 95 wt. %, from about 50 wt. % to about 95 wt. %, from about 60 wt. % to about 95 wt. %, from about 70 wt. % to about 95 wt. %, from about 80 wt. % to about 95 wt. %, from about 90 wt. % to about 95 wt. %, from about 1 wt. % to about 90 wt. %, from about 2 wt. % to about 90 wt. %, from about 3 wt. % to about 90 wt. %, from about 4 wt. % to about 90 wt. %, from about 5 wt. % to about 90 wt. %, from about 10 wt. % to about 90 wt. %, from about 15 wt. % to about 90 wt. %, from about 20 wt. % to about 90 wt. %, from about 25 wt. % to about 90 wt. %, from about 30 wt. % to about 90 wt. %, from about 35 wt. % to about 90 wt. %, from about 40 wt. % to about 90 wt. %, from about 45 wt. % to about 90 wt. %, from about 50 wt. % to about 90 wt. %, from about 60 wt. % to about 90 wt. %, from about 70 wt. % to about 90 wt. %, or from about 80 wt. % to about 90 wt. % of the metal oxide on the catalyst support. In certain embodiments, the metal oxide on the catalyst support of the pyrolysis catalyst consists of tungsten oxide and/or molybdenum oxide.

The pyrolysis catalyst can have a metal oxide loading of about 0.1 wt. % or greater, about 0.5 wt. % or greater, about 1 wt. % or greater, about 2 wt. % or greater, about 5 wt. % or greater, about 10 wt. % or greater, about 20 wt. % or greater, about 30 wt. % or greater, about 40 wt. % or greater, about 50 wt. % or greater, about 60 wt. % or greater, about 70 wt. % or greater, about 80 wt. % or greater, about 90 wt. % or greater, about 95 wt. % or greater, or about 99 wt. % or greater. For example, in various embodiments, the pyrolysis catalyst has a metal oxide loading of from about 0.1 wt. % to about 15 wt. %, from about 0.5 wt. % to about 15 wt. %, from about 1 wt. % to about 15 wt. %, from about 2 wt. % to about 15 wt. %, from about 5 wt. % to about 15 wt. %, from about 0.1 wt. % to about 10 wt. %, from about 0.5 wt. % to about 10 wt. %, from about 1 wt. % to about 10 wt. %, from about 2 wt. % to about 10 wt. %, or from about 5 wt. % to about 10 wt. %.

In some cases, it has been found that low surface area pyrolysis catalysts and catalyst supports provide for greater product yields (e.g., greater yields of glycolaldehyde). Accordingly, in some embodiments, the pyrolysis catalyst support comprises a material that has a relatively low surface area (e.g., a BET specific surface area of about 500 $m^2/g$ or less, about 250 $m^2/g$ or less, about 100 $m^2/g$ or less, about 50 $m^2/g$ or less, about 25 $m^2/g$ or less, about 10 $m^2/g$ or less, about 5 $m^2/g$ or less, or about 1 $m^2/g$ or less).

In various embodiments, the pyrolysis catalyst support comprises a material selected from the group consisting of glass, ceramic, refractory material, and mixtures thereof. In some embodiments, the pyrolysis catalyst support comprises a glass material. In certain embodiments, the glass material comprises glass beads (e.g., glass spheres or similar geometric or amorphous shapes). In some embodiments, the pyrolysis catalyst support comprises a ceramic material selected from the group consisting of silicon carbide, yttria-stabilized zirconia, and combinations thereof. In certain embodiments, the pyrolysis catalyst support comprises a material that is substantially nonporous and has a relatively low surface area.

The pyrolysis catalysts described herein and more fully described and exemplified in the commonly-assigned, concurrently-filed application we have referenced above can provide for an extended time on stream (TOS) period. In some embodiments, the TOS of the catalyst is about 1,500 hours or greater, about 2,000 hours or greater, about 4,000 hours or greater, about 6,000 hours or greater, about 8,000 hours or greater, or about 10,000 hours or greater.

The pyrolysis catalyst can be prepared according to processes as described further herein. In some embodiments, the pyrolysis catalyst comprises a glass material and a coating comprising the metal oxide and the coating is deposited on the glass material coated using a sol-gel comprising the metal oxide or reaction product thereof. In these and other embodiments, the pyrolysis catalyst is an uncalcined pyrolysis catalyst.

Pyrolysis is an energy intensive process requiring elevated temperatures in the pyrolysis reaction zone. In various embodiments, the pyrolysis reaction zone is heated to a temperature of about 400° C. or greater, about 450° C. or greater, about 475° C. or greater, about 500° C. or greater, about 525° C. or greater, about 550° C. or greater, about 575° C. or greater, or about 600° C. or greater. In some embodiments, the pyrolysis reaction zone is heated to a temperature of from about 400° C. to about 600° C., from about 400° C. to about 575° C., from about 400° C. to about 550° C., from about 400° C. to about 525° C., from about 450° C. to about 600° C. from about 450° C. to about 575° C., from about 450° C. to about 550° C., from about 450° C. to about 525° C., from about 500° C. to about 600° C., from about 500° C. to about 575° C., from about 500° C. to about 550° C., from about 500° C. to about 525° C., from about 525° C. to about 600° C., from about 525° C. to about 575° C., or from about 525° C. and about 550° C.

In addition to the pyrolysis catalyst comprising a metal oxide on a catalyst support, the pyrolysis reaction zone can further comprise a reaction zone media that is different than the catalyst. In various embodiments, the reaction zone media can include any inert material with which the pyrolysis catalyst can be combined and fluidized to provide a generally homogeneously distributed fluidized bed through which a carbohydrate feed composition and pyrolysis products may be carried as they are formed by an inert carrier gas, and which can be used to convey the thermal energy necessary to pyrolyze the carbohydrates in the carbohydrate feed and convert the carbohydrate(s) to pyrolysis products inclusive at least of glycolaldehyde. Those of skill in the art will be well able to identify a variety of materials that would be able to perform these essential functions. In various embodiments, the reaction zone media comprises a material selected from the group consisting of glass, ceramic, refractory material, and mixtures thereof. In some embodiments, the reaction zone media comprises a glass material. In some embodiments, the reaction zone media comprises a ceramic material selected from the group consisting of silicon carbide, yttria-stabilized zirconia, and combinations thereof. In certain embodiments, the glass material comprises glass beads (e.g., glass spheres or similar geometric or amorphous shapes) and/or sand.

As noted, the reaction zone media is typically different than the pyrolysis catalyst comprising a metal oxide on a support. Accordingly, in various embodiments, the reaction zone media is uncoated. In certain embodiments, the reaction zone media is free or essentially free (e.g., less than 1 wt. % or even less than 0.1 wt. %) of a metal oxide coating. In some embodiments, the reaction zone media comprises the support of the catalyst without metal oxide (i.e., the bare pyrolysis catalyst support).

The pyrolysis catalyst and reaction zone media can constitute a total volume of media loaded within the pyrolysis reaction zone, such that the catalyst is from about 1 vol. % to about 50 vol. %, from about 2 vol. % to about 25 vol. %, from about 3 vol. % to about 15 vol. %, or from about 4 vol. % to about 10 vol. % of the total volume of media loaded within the pyrolysis reaction zone.

In various embodiments, the pyrolysis feed composition is fluidized in a fluidizing or carrier gas in the pyrolysis reaction zone. Fluidizing gases include, for example, various inert gases or inert gas mixtures. In some embodiments, the fluidizing gas comprises nitrogen, steam, carbon dioxide, and/or waste gases such as combustion off-gas. In some embodiments, e.g., wherein the carbohydrate is provided in the form of a carbohydrate solution, the pyrolysis process further comprises atomizing the feed composition fed to the pyrolysis reaction zone. In certain embodiments, the pyrolysis feed composition can be atomized using a fluidizing gas (e.g., nitrogen, steam, etc.).

The average residence time of the carbohydrate feed in the pyrolysis reaction zone can be relatively fast. For example, in some embodiments the residence time is about 10 seconds or less, about 8 seconds or less, about 6 seconds or less, about 4 seconds or less, about 2 seconds or less, about 1 second or less, or about 0.5 seconds or less. In certain embodiments, the residence time is from about 0.5 seconds to about 10, from about 0.5 seconds to about 5 seconds, from about 0.5 seconds to about 2 seconds, from about 0.5 seconds to about 1 second, from about 1 second to about 10, from about 1 second to about 5 seconds, or from about 1 second to about 2 seconds.

In general, the pyrolysis reaction zone can include one or more batch, semi-batch, or continuous reactor designs using fixed bed reactors, trickle bed reactors, slurry phase reactors, moving bed reactors, or any other design that allows for catalytic reactions, particularly heterogeneous catalytic reactions. Examples of reactors can be seen in *Chemical Process Equipment—Selection and Design*, Couper et al., Elsevier 1990, which is incorporated herein by reference. In various processes described herein, the pyrolysis reaction zone comprises one or more fluidized bed reactors. It should be understood that feed compositions, any fluidizing gas, and catalysts can be introduced into a suitable reactor separately or in various combinations.

The improved pyrolysis processes summarized herein have been found to provide for enhanced product yields. For example, various pyrolysis processes described herein, as demonstrated herein using a 20 wt. % aqueous glucose solution as the carbohydrate feed, provide a yield of glycolaldehyde that is about 70% or greater, about 75% or greater, or about 80% or greater. In some embodiments, the yield of glycolaldehyde is from about 70% to about 85%, from about 70% to about 80%, from about 75% to about 85%, or from about 75% to about 80%.

The pyrolysis reaction product can further comprise other minor components. In various embodiments, the pyrolysis reaction product comprises at least one other component selected from the group consisting of formaldehyde, glyoxal, pyruvaldehyde, acetol, and mixtures thereof. In some embodiments, the pyrolysis reaction product further comprises formaldehyde. In certain embodiments, the pyrolysis reaction product further comprises formaldehyde and the molar ratio of glycolaldehyde to formaldehyde is about 5:1 or greater, about 6:1 or greater, about 8:1 or greater, about 10:1 or greater, or about 12:1 or greater.

In various embodiments, the pyrolysis reaction product further comprises glyoxal. In some embodiments, the pyrolysis reaction product further comprises glyoxal and the molar ratio of glycolaldehyde to glyoxal is about 10:1 or greater, about 15:1 or greater, about 20:1 or greater, or about 25:1 or greater.

In various embodiments, the pyrolysis reaction product further comprises pyruvaldehyde. In some embodiments, the pyrolysis reaction product further comprises pyruvaldehyde and the molar ratio of glycolaldehyde to pyruvaldehyde is about 5:1 or greater, about 6:1 or greater, about 8:1 or greater, about 10:1 or greater, or about 12:1 or greater.

In various embodiments, the pyrolysis reaction product further comprises acetol. In some embodiments, the pyrolysis reaction product further comprises acetol and the molar ratio of glycolaldehyde to acetol is about 15:1 or greater, about 20:1 or greater, about 25:1 or greater, or about 30:1 or greater.

In various embodiments, the pyrolysis reaction product is free or essentially free of ethylene glycol. In some embodiments, the molar ratio of glycolaldehyde to ethylene glycol in the pyrolysis reaction product is about 100:1 or greater; about 200:1 or greater; or about 400:1 or greater.

The processes of the present invention for forming the $C_4$ aldoses and/or ketones can thus include various combinations of features, as described herein. For example, various processes can further comprise preparing glycolaldehyde by steps comprising:

feeding a feed composition comprising a carbohydrate having at least four carbon atoms to a pyrolysis reaction zone; and pyrolyzing the carbohydrate in the presence of water and a catalyst in the pyrolysis reaction zone to form a reaction product comprising glycolaldehyde, wherein the catalyst comprises a metal oxide on a catalyst support and at least one of the following conditions is satisfied:

(a) the pyrolysis reaction zone is heated to a temperature of about 400° C. or greater;

(b) the catalyst support has a BET specific surface area that is about 500 $m^2/g$ or less, about 250 $m^2/g$ or less, about 100 $m^2/g$ or less, about 50 $m^2/g$ or less, about 25 $m^2/g$ or less, about 10 $m^2/g$ or less, about 5 $m^2/g$ or less, or about 1 $m^2/g$ or less;

(c) the catalyst support comprises a glass material;

(d) the pyrolysis reaction zone further comprises a reaction zone media that is different than the catalyst; and/or (e) the yield of glycolaldehyde is about 70% or greater, about 75% or greater, or about 80% or greater.

The pyrolysis catalyst can be prepared by various techniques. The metal oxide can be deposited on the catalyst supports using procedures including, but not limited to sol-gel, incipient wetness, ion-exchange, deposition-precipitation, and vacuum impregnation techniques.

One process for preparing a pyrolysis catalyst that has been found to be particularly effective comprises:

mixing a metal oxide, a solvent, and a strong acid to form a sol-gel;

depositing the sol-gel on a pyrolysis catalyst support to form a coated catalyst support;

and removing solvent from the coated catalyst support to form the pyrolysis catalyst.

In some embodiments, the sol-gel is prepared by mixing a metal oxide, a peroxide source and a solvent. In further embodiments, the peroxide source comprises hydrogen peroxide and the solvent comprises water.

The metal oxide, metal oxide loading, and support can be any of those as specified herein for the pyrolysis catalyst. For example, in some embodiments, the metal oxide can comprise tungsten oxide and/or molybdenum oxide and the support can comprise a low surface area material such as glass (e.g., glass beads).

In various embodiments, the solvent comprises a $C_1$-$C_{10}$ alkanol. For example, the $C_1$-$C_{10}$ alkanol is selected from the group consisting of isopropanol, ethanol, and mixtures thereof. Further, the strong acid can be selected from the group consisting of hydrochloric acid, sulfuric acid, nitric acid, and mixtures thereof.

The sol-gel may be formed in air or it may be formed in an inert atmosphere. In some embodiments, the sol-gel is formed in an inert atmosphere. For example, the sol-gel can be formed in a nitrogen atmosphere. Further, the sol-gel can be formed in the substantial absence of oxygen. In various embodiments the sol-gel can be prepared by mixing a metal oxide, a peroxide source and a solvent. In some embodiments the peroxide source may be hydrogen peroxide and the solvent may be water.

During solvent removal, the coated catalyst support can be heated to a temperature sufficient to vaporize any solvent on the coated catalyst. In various embodiments, the coated catalyst support is heated to a temperature of about 80° C. or greater, about 90° C. or greater, or about 100° C. or greater to remove solvent. However, in various embodiments, the catalyst is not subjected to temperatures typical of calcination (e.g., about 500° C. or greater, about 750° C. or greater, or about 1000° C. or greater).

Downstream Processes

The processes of the present invention also include integrated processes comprising additional steps to convert the $C_4$ aldose and/or ketone thereof to a downstream product. For example, various processes are directed to preparing erythritol and/or threitol. In some embodiments, these processes comprise preparing erythrose and/or threose according to the condensation processes as described herein (e.g., contacting a feed composition comprising glycolaldehyde with a catalyst comprising an imidazolate framework in a reaction zone to condense at least a portion of the glycolaldehyde to erythrose and threose); and hydrogenating at least a portion of the erythrose and/or threose to form the erythritol and/or threitol. Suitable methods for the hydrogenation of erythrose and threose to form erythritol and threitol, respectively, are known to those of skill in the art, see, for example, U.S. Pat. Nos. 4,487,980 and 6,300,494, all of which are hereby incorporated by reference. A preferred method for the formation of these sugar alcohols would be as described in commonly-assigned U.S. Pat. No. 10,196,333 to Werpy et al., "Multiphase Low Mixing Processes", which is incorporated by reference herein.

Other processes are directed to preparing erythronic acid, threonic acid, and/or a salt thereof. In various embodiments, these processes comprise preparing erythrose and/or threose according to the condensation processes as described herein (e.g., contacting a feed composition comprising glycolaldehyde with a catalyst comprising an imidazolate framework in a reaction zone to condense at least a portion of the glycolaldehyde to erythrose and threose); and oxidizing at least a portion of the erythrose and/or threose to form the erythronic acid, threonic acid, and/or salt thereof. Suitable methods for the oxidation of erythrose and/or threose are also known, see, for example, U.S. Patent Application Publication 2007/0027341, which is hereby incorporated by reference.

Further integrated processes are directed to preparing a downstream product such as glyceraldehyde; methyl vinyl glycolate; 2-hydroxy-4-methoxybutanoate; 2-hydroxy-4-methoxybutanoic acid; 1,4-butandiol; α-hydroxy-γ-butyrolactone, methionine, and analogues thereof. In some embodiments, these process comprise preparing a $C_4$ aldose and/or ketone thereof according to the processes described herein (e.g., contacting a feed composition comprising glycolaldehyde with a catalyst comprising an imidazolate framework in a reaction zone to condense at least a portion of the glycolaldehyde to the $C_4$ aldose and/or ketone thereof); and converting the $C_4$ aldose and/or ketone thereof to a downstream product or a precursor thereof, wherein the downstream product is a compound selected from the group consisting of glyceraldehyde; methyl vinyl glycolate; 2-hydroxy-4-methoxybutanoate; 2-hydroxy-4-methoxybutanoic acid; 1,4-butandiol; α-hydroxy-γ-butyrolactone, methionine, and analogues thereof. Methods for forming each of these downstream products or a precursor thereof from a $C_4$ aldose and/or ketone thereof are known already, see, for example, Holm et al., Green Chemistry (2012) 14, pp 702-706 (methyl vinyl glycolate; 2-hydroxy-4-methoxybutanoate; and 2-hydroxy-4-methoxybutanoic acid), Amada et al., (2012), ChemSusChem, 5:1991-1999 (1,4-butandiol); Dusselier et al, ACS Catal., 2013, 3 (8), pp 1786-1800 (α-hydroxy-γ-butyrolactone); U.S. Pat. No. 10,189,778 (methionine) all of which are incorporated by reference herein.

In general, the reaction zones can include one or more batch, semi-batch, or continuous reactor designs using fixed bed reactors, trickle bed reactors, slurry phase reactors, moving bed reactors, fluidized bed reactors or any other design that allows for catalytic reactions, particularly heterogeneous catalytic reactions. Examples of such reactors can be seen in *Chemical Process Equipment—Selection and Design*, Couper et al., Elsevier 1990, which is incorporated herein by reference.

The processes of the present invention can include various combinations of features as described herein.

Having described the invention in detail, it will be apparent that modifications and variations are possible without departing from the scope of the invention defined in the appended claims.

EXAMPLES

The following non-limiting examples are provided to further illustrate the present invention.

Example 1: Preparing a Metal Oxide-Coated Glass Bead Catalyst

To prepare a metal oxide-coated glass bead catalyst, a metal oxide sol-gel was first prepared in a nitrogen-filled environment to prevent exposure to oxygen. 0.70 mL of a tungsten (V) ethoxide, 1,2-dimethoxyethane adduct, 99%, was added to 50 mL of isopropanol, while stirring. 0.2 mL of 2 M hydrochloric acid was then added in a dropwise manner, resulting in a pale-yellow sol containing a white precipitate. The mixture was stirred at room temperature for approximately one hour and allowed to rest overnight.

Glass beads were prepared by fuming the beads with isopropanol. 25 ml of the fumed beads were then added to the sol. The mixture containing the beads was mixed periodically and left uncovered. The resulting coated glass beads were evenly coated with the tungsten oxide solution.

The coated glass beads were then dried at ambient temperature and subjected to heat of approximately 80° C. overnight. The coated glass beads were not subjected to calcination or otherwise modified.

Each coated glass bead comprised approximately 0.25 wt. % tungsten in the form of a thin-film coating.

Example 2: Preparing a Metal Oxide-Coated Glass Bead Catalyst

An experiment following the procedure of Example 1 was performed, except that the coated glass beads were rinsed in acetone prior to heating at approximately 80° C. overnight. Rinsing the coated glass beads with acetone did not remove any meaningful amount of the tungsten oxide solution.

Example 3: Pyrolysis of Dextrose Utilizing a Glass Bead Catalyst

Untreated glass bead catalysts were tested for pyrolysis of dextrose utilizing a fluidized bed reactor system. The glass bead catalysts represented 6% of the total media volume of the reactor bed. An approximately 20 wt. % dextrose solution was introduced into the reactor system at a rate of 1.7 mL/min. A nitrogen gas stream was also directed into the system at a rate of 4500-5000 mL/min. Tables 1-3, below, report the product profile at various time on stream for differing reaction temperatures. Each of the reactions set forth below had a 0.98 s residence time.

TABLE 1

| Reaction at 525° C. | | | | | | | | |
|---|---|---|---|---|---|---|---|---|
| Run | Time on Stream (hours) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R40-22-24 | 24 | 72.974 | 3.917 | 1.928 | 8.490 | 7.397 | — | — |
| R40-22-27 | 27 | 72.313 | 3.592 | 2.633 | 7.889 | 4.217 | 1.240 | 1.335 |
| R40-22-44 | 44 | 72.128 | 4.667 | 2.283 | 7.684 | 5.125 | — | — |

TABLE 2

| Reaction at 550° C. | | | | | | | | | |
|---|---|---|---|---|---|---|---|---|---|
| Run | Time on Stream (hours) | Glucose (wt. %) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R59-22 19 | 19 | 0.23 | 70.49 | 8.88 | 2.69 | 7.98 | 3.13 | 1.19 | 3.55 |
| R59-22-20 | 20 | 0.08 | 69.94 | 8.68 | 2.79 | 7.67 | 2.56 | 1.5 | 3.25 |
| R59-22-22 | 22 | 0 | 70.62 | 9.07 | 2.73 | 8.06 | 2.89 | 1.93 | 3.91 |
| R59-22-24 | 24 | 0 | 67.22 | 9.54 | 2.89 | 7.73 | 3.31 | 1.78 | 4.05 |
| R59-22-25 | 25 | 0.04 | 69.81 | 8.41 | 2.9 | 7.63 | 2.8 | 1.48 | 3.57 |
| R59-22-43 | 43 | 0 | 71.21 | 7.59 | 2.74 | 7.91 | 2.87 | 1.17 | 3.04 |

TABLE 2-continued

| Reaction at 550° C. | | | | | | | | | |
|---|---|---|---|---|---|---|---|---|---|
| Run | Time on Stream (hours) | Glucose (wt. %) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R59-22-47 | 47 | 0.16 | 72.01 | 8.63 | 3.02 | 8.19 | 3.5 | 1.64 | 2.28 |
| R59-22-48 | 48 | 0 | 71.79 | 8.6 | 2.99 | 7.53 | 3.66 | 1.31 | 3.14 |

TABLE 3

| Reaction at 550° C. | | | | | | | | | |
|---|---|---|---|---|---|---|---|---|---|
| Run | Time on Stream (hours) | Glucose (wt. %) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R61-22-4 | 4 | 0 | 67.68 | 8.94 | 2.42 | 8.19 | 3.53 | — | — |
| R61-22-26 | 26 | 0 | 67.92 | 8.04 | 2.38 | 7.55 | 3.21 | 2.31 | 6.21 |
| R61-22-29 | 29 | 0.2 | 68.71 | 8.73 | 2.37 | 7.94 | 3.41 | 2.3 | 6.69 |
| R61-22-96 | 96 | 0 | 22.44 | 9.41 | 1.13 | 7.87 | 2.71 | 4.15 | 10.32 |

Example 4: Pyrolysis of Dextrose Utilizing Tungsten Carbide

A tungsten carbide grit material was mixed with glass beads and utilized in a fluidized bed reactor system for the pyrolysis or cracking of dextrose. The mixture was tested at varying reactor temperatures and compared to the experiment run with uncoated glass beads.

An approximately 20 wt. % dextrose solution was introduced into the reactor system at a rate of 1.7 mL/min. A nitrogen gas stream was also directed into the system at a rate of 4500-5000 mL/min. Tables 4 and 5 report the temperature at various points in the reactor system, flow rates, residence time, etc. The "Bottom Temperature" reported below is the temperature at the feed nozzle of the fluidized bed reactor. Table 6 reports the product profile for a given time on stream.

TABLE 4

| Run | Time On Stream (hours) | Set Temp. (° C.) | Top Temp. (° C.) | Upper Middle Temp. (° C.) | Middle Temp. (° C.) | Bottom Temp. (° C.) | Liquid Feed Flow Rate (ml/min) | $N_2$ Flow Rate Nozzle (ml/min) | $N_2$ Flow Rate Reactor (ml/min) |
|---|---|---|---|---|---|---|---|---|---|
| R50-22-1 | 1 | 500.0 | 546.7 | 571.8 | 549.4 | 1140.0 | 1.7 | 4493.4 | 0.0 |
| R50-22-3 | 3 | 500.0 | 523.3 | 525.5 | 612.4 | 1140.0 | 1.7 | 4992.6 | 0.0 |
| R50-22-7 | 7 | 475.0 | 499.9 | 506.5 | 585.0 | 1140.0 | 1.7 | 4992.8 | 1598.4 |
| R50-22-23 | 23 | 475.0 | 500.9 | 510.0 | 581.1 | 1140.0 | 1.7 | 4993.4 | 1598.9 |
| R50-22-27 | 27 | 475.0 | 501.7 | 519.0 | 575.5 | 1140.0 | 2.0 | 4992.2 | 1598.9 |
| R50-22-29 | 29 | 460.0 | 484.9 | 501.5 | 556.5 | 1140.0 | 1.7 | 4992.0 | 1599.0 |

TABLE 5

| Run | Time On Stream (hours) | Residence Time (s) | Mass Collected (g) | % Recovery |
|---|---|---|---|---|
| R50-22-1 | 1 | 1.044 | 15.814 | 92.37 |
| R50-22-3 | 3 | 0.967 | 16.011 | 93.52 |
| R50-22-7 | 7 | 0.809 | 15.871 | 92.70 |
| R50-22-23 | 23 | 0.809 | 16.039 | 93.9 |
| R50-22-27 | 27 | 0.772 | 20.502 | 97.43 |
| R50-22-29 | 29 | 0.825 | 16.029 | 93.63 |

TABLE 6

| Run | Time On Stream (hours) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
|---|---|---|---|---|---|---|---|---|
| R50-22-1 | 1 | 51.98 | 8.22 | 2.19 | 6.82 | 2.65 | 6.58 | 4.86 |
| R50-22-3 | 3 | 51.36 | 8.41 | 3.28 | 7.10 | 2.19 | 6.31 | 3.78 |
| R50-22-7 | 7 | 60.95 | 9.89 | 2.48 | 7.61 | 1.70 | 3.20 | 2.09 |
| R50-22-23 | 23 | 63.81 | 8.87 | 2.30 | 7.55 | 1.62 | 2.08 | 2.32 |
| R50-22-27 | 27 | 67.08 | 10.23 | 2.18 | 7.81 | 1.63 | 1.87 | 1.92 |
| R50-22-29 | 29 | 63.53 | 8.73 | 1.89 | 7.69 | 1.57 | 2.31 | 1.66 |

A second experiment utilizing tungsten carbide grit material mixed with glass beads was conducted under the same conditions. The cracking media comprised approximately 3% tungsten carbide grit and 97% glass beads, on a volume basis. Tables 7 and 8 report the temperature at various points in the reactor system, flow rates, residence time, etc. The product profile of this second experiment is reported below in Table 9.

| Run | Time On Stream (hours) | Set Temp. (° C.) | Liquid Feed Flow Rate (ml/min) | $N_2$ Flow Rate Nozzle (ml/min) | $N_2$ Flow Rate Reactor (ml/min) |
|---|---|---|---|---|---|
| R51-22-3 | 3 | 525.0 | 1.7 | 4993.2 | −44.4 |
| R51-22-6 | 6 | 475.0 | 2.1 | 4992.6 | 1598.6 |
| R51-22-23 | 23 | 475.0 | 2.1 | 4993.0 | 1599.2 |
| R51-22-26 | 26 | 475.0 | 2.1 | 4992.7 | 1598.8 |

TABLE 8

| Run | Time On Stream (hours) | Residence Time (s) | Mass Collected (g) | % Recovery |
|---|---|---|---|---|
| R51-22-3 | 3 | 0.938 | 16.179 | 94.50 |
| R51-22-6 | 6 | 0.770 | 19.906 | 93.02 |
| R51-22-23 | 23 | 0.770 | 19.830 | 92.66 |
| R51-22-26 | 26 | 0.770 | 19.933 | 93.15 |

TABLE 9

| Run | Time On Stream (hours) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
|---|---|---|---|---|---|---|---|---|
| R51-22-3 | 3 | 63.28 | 8.73 | 2.34 | 8.48 | 3.10 | 2.21 | 4.25 |
| R51-22-6 | 6 | 65.13 | 8.37 | 1.54 | 11.06 | 2.96 | 1.57 | 1.68 |
| R51-22-23 | 23 | 66.05 | 9.88 | 1.65 | 10.47 | 2.79 | 0.72 | 1.07 |
| R51-22-26 | 26 | 66.07 | 8.01 | 1.57 | 10.19 | 2.87 | 1.05 | 1.62 |

Example 5: Pyrolysis of Dextrose Utilizing a Tungsten Oxide-Coated Glass Bead Catalyst Several experiments similar to those conducted in Example 4 were performed. Tables 10 and 11 report the results using tungsten oxide coated glass bead catalysts at varying temperatures of the reactor system, wherein the tungsten oxide-coated catalysts represented approximately 6 wt. % of the total cracking media.

TABLE 10

| Tungsten Oxide Catalyst | | | | | | | | | | |
|---|---|---|---|---|---|---|---|---|---|---|
| Run | Time on Stream (hours) | Temp. (° C.) | Glucose (wt. %) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R62-22-1 | 1 | 550 | 0 | 59.54 | 9.22 | 3 | 8.65 | 3.38 | 0 | 0 |
| R62-22-2 | 2 | 550 | 0.08 | 66.21 | 8.18 | 3.19 | 8.63 | 2.78 | 1.62 | 6.45 |
| R62-22-20 | 20 | 550 | 0 | 75.21 | 8.33 | 3.15 | 8.26 | 2.95 | 1.57 | 4.78 |
| R62-22-23 | 23 | 550 | 0.09 | 76.95 | 8.05 | 3.04 | 7.93 | 2.72 | 1.17 | 4.06 |
| R62-22-43 | 43 | 525 | 0 | 76.6 | 5.99 | 3.07 | 7.54 | 2.4 | 0.63 | 3.48 |
| R62-22-46 | 46 | 525 | 0.16 | 81.78 | 7.38 | 3.6 | 8.64 | 2.22 | 0.71 | 3.74 |
| R62-22-62 | 62 | 525 | 0.17 | 80.89 | 7.06 | 3.25 | 7.89 | 2.32 | 0 | 0 |

TABLE 11

| Tungsten Oxide Catalyst | | | | | | | | | | |
|---|---|---|---|---|---|---|---|---|---|---|
| Run | Time on Stream (hours) | Temp. (° C.) | Glucose (wt. %) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R60-22-3 | 3 | 550 | 0.11 | 71.47 | 10.15 | 3.22 | 9.17 | 3.77 | 1.15 | 4.16 |
| R60-22-22 | 22 | 550 | 0 | 74.82 | 8.68 | 3.18 | 8.61 | 2.68 | 0.99 | 4.42 |
| R60-22-46 | 46 | 550 | 0 | 74.98 | 8.6 | 3.09 | 8.4 | 2.48 | 0.69 | 4.17 |
| R60-22-52 | 52 | 550 | 0 | 75.39 | 8.99 | 3.13 | 8.71 | 2.49 | 0.72 | 4.02 |
| R60-22-119 | 119 | 550 | 0 | 67.78 | 10.42 | 2.61 | 9.63 | 3.3 | 1.64 | 6 |
| R60-22-120 | 120 | 550 | 0.07 | 71.9 | 9.21 | 3.09 | 9.07 | 3.35 | 1.25 | 4.66 |
| R60-22-142 | 142 | 550 | 0 | 78.56 | 9.02 | 3.1 | 9.02 | 3.26 | 1.05 | 4.38 |
| R60-22-143 | 143 | 525 | 0 | 74.27 | 8.82 | 2.92 | 9.19 | 2.91 | 1.27 | 2.23 |
| R60-22-144 | 144 | 525 | 0.1 | 75.8 | 8 | 2.98 | 9.07 | 2.47 | 1.22 | 1.88 |
| R60-22-146 | 146 | 525 | 0 | 74.9 | 8.45 | 2.73 | 9.13 | 2.87 | 1.36 | 3.18 |
| R60-22-147 | 147 | 525 | 0 | 76.4 | 8.35 | 2.94 | 9.17 | 2.76 | 2.3 | 2.39 |
| R60-22-148 | 148 | 525 | 0.16 | 77.96 | 8.46 | 2.93 | 9.01 | 2.83 | 1.04 | 2.46 |

TABLE 11-continued

| Tungsten Oxide Catalyst | | | | | | | | | | |
|---|---|---|---|---|---|---|---|---|---|---|
| Run | Time on Stream (hours) | Temp. (° C.) | Glucose (wt. %) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
| R60-22-165 | 165 | 525 | 0.06 | 78.02 | 8.28 | 2.84 | 8.42 | 2.45 | 0.9 | 2.72 |
| R60-22-167 | 167 | 500 | 0 | 79.2 | 8.47 | 2.98 | 9.21 | 2.49 | 0.85 | 3.18 |
| R60-22-169 | 169 | 500 | 0 | 77.67 | 10.23 | 2.89 | 10.09 | 3.18 | 0.88 | 2.29 |

As demonstrated by the above results, a catalyst comprising metal oxide-coated glass beads produced a considerably higher yield of glycolaldehyde as compared to a metal carbide catalyst.

Example 6: Pyrolysis of Dextrose Utilizing a Molybdenum Oxide-Coated Glass Bead Catalyst A similar experiment to Example 4 was performed using a molybdenum oxide-coated glass bead catalyst that represented approximately 6 wt. % of the total cracking media. The catalyst was tested at varying reactor temperatures. The reaction conditions are set forth in Table 12 and the results are reported in Table 13.

TABLE 12

| Run | Time on Stream (hours) | $N_2$ Flow Rate (ml/min) | Feed Flow Rate (ml/min) | Temp. (° C.) | Residence Time (Sec) | Mass Collected (g) | % Recovery |
|---|---|---|---|---|---|---|---|
| R70-22-2 | 2 | 4673.46 | 1.65 | 525 | 0.981 | 16.2205 | 94.75 |
| R70-22-5 | 5 | 4672.95 | 1.65 | 525 | 0.981 | 16.4251 | 95.94 |
| R70-22-23 | 23 | 4673.36 | 1.65 | 525 | 0.981 | 16.5128 | 96.45 |
| R70-22-30 | 30 | 4653.02 | 1.65 | 525 | 0.984 | 16.7143 | 97.63 |
| R70-22-47 | 47 | 4722.83 | 1.65 | 525 | 0.973 | 16.7549 | 97.87 |
| R70-22-53 | 53 | 4852.57 | 1.65 | 525 | 0.986 | 16.7271 | 97.71 |

TABLE 12-continued

| Run | Time on Stream (hours) | $N_2$ Flow Rate (ml/min) | Feed Flow Rate (ml/min) | Temp. (° C.) | Residence Time (Sec) | Mass Collected (g) | % Recovery |
|---|---|---|---|---|---|---|---|
| R70-22-122 | 122 | 4652.67 | 1.65 | 525 | 0.984 | 16.8052 | 98.16 |
| R70-22-144 | 144 | 4652.33 | 1.65 | 525 | 0.986 | 16.9679 | 99.11 |
| R70-22-169 | 169 | 4652.48 | 1.65 | 525 | 0.985 | 17.1050 | 99.91 |
| R70-22-193 | 193 | 4652.84 | 1.65 | 525 | 0.985 | 16.9095 | 98.77 |
| R70-22 197 | 197 | 4652.77 | 1.65 | 525 | 0.985 | 16.6974 | 97.53 |
| R70-22-217 | 217 | 4653.05 | 1.65 | 525 | 0.983 | 16.6044 | 96.99 |
| R70-22-289 | 289 | 4652.82 | 1.65 | 525 | 0.985 | 16.7214 | 97.67 |
| R70-22-337 | 337 | 4652.69 | 1.65 | 525 | 0.985 | 16.8754 | 98.57 |
| R70-22-366 | 366 | 4652.81 | 1.65 | 525 | 0.984 | 16.8459 | 98.40 |
| R70-22-457 | 457 | 4652.75 | 1.65 | 525 | 0.985 | 16.6437 | 97.22 |
| R70-22-506 | 506 | 4652.87 | 1.65 | 525 | 0.981 | 16.2371 | 94.84 |
| R70-22-672 | 672 | 4652.32 | 1.65 | 525 | 0.985 | 16.3954 | 95.77 |

TABLE 13

| Run | Time on Stream (hours) | Temp. (° C.) | Glucose (wt. %) | Glycol-aldehyde (wt. %) | Form-aldehyde (wt. %) | Glyoxal (wt. %) | Pyruv-aldehyde (wt. %) | Acetol (wt. %) |
|---|---|---|---|---|---|---|---|---|
| R70-22-2 | 2 | 525 | 0.05 | 66.01 | 9.43 | 4.54 | 9.42 | 2.30 |
| R70-22-5 | 5 | 525 | 0.06 | 73.79 | 8.27 | 4.45 | 9.17 | 1.81 |
| R70-22-23 | 23 | 525 | 0.15 | 76.99 | 7.42 | 4.26 | 8.68 | 1.51 |
| R70-22-30 | 30 | 525 | 0.12 | 79.36 | 8.13 | 4.27 | 9.15 | 1.66 |

TABLE 13-continued

| Run | Time on Stream (hours) | Temp. (° C.) | Glucose (wt. %) | Glycol-aldehyde (wt. %) | Form-aldehyde (wt. %) | Glyoxal (wt. %) | Pyruv-aldehyde (wt. %) | Acetol (wt. %) |
|---|---|---|---|---|---|---|---|---|
| R70-22-47 | 47 | 525 | 0.13 | 78.66 | 8.21 | 4.25 | 9.09 | 1.61 |
| R70-22-53 | 53 | 525 | 0.15 | 79.83 | 7.65 | 3.61 | 8.68 | 1.20 |
| R70-22-122 | 122 | 525 | 0.07 | 79.86 | 7.87 | 4.12 | 9.03 | 1.58 |
| R70-22-144 | 144 | 525 | 0.00 | 79.76 | 7.74 | 4.34 | 8.74 | 1.56 |
| R70-22-169 | 169 | 525 | 0.06 | 80.01 | 7.33 | 3.96 | 8.53 | 1.63 |
| R70-22-193 | 193 | 525 | 0.10 | 80.11 | 7.29 | 4.01 | 8.51 | 1.53 |
| R70-22-197 | 197 | 525 | 0.00 | 78.45 | 8.85 | 4.60 | 10.02 | 1.54 |
| R70-22-217 | 217 | 525 | 0.06 | 81.19 | 8.11 | 4.15 | 9.28 | 1.58 |
| R70-22-289 | 289 | 525 | 0.06 | 80.14 | 5.99 | 3.31 | 8.13 | 1.49 |
| R70-22-337 | 337 | 525 | 0.00 | 82.40 | 8.44 | 4.20 | 9.48 | 1.48 |
| R70-22-366 | 366 | 525 | 0.07 | 82.31 | 8.30 | 3.92 | 9.53 | 1.56 |
| R70-22-457 | 457 | 525 | 0.12 | 83.69 | 7.92 | 3.92 | 9.75 | 1.46 |
| R70-22-506 | 506 | 525 | 0.00 | 85.27 | 8.51 | 4.05 | 9.87 | 1.66 |
| R70-22-672 | 672 | 525 | 0.05 | 66.01 | 9.43 | 4.54 | 9.42 | 2.30 |

Example 7: Pyrolysis of Dextrose Utilizing a Vanadium Oxide-Coated Glass Bead Catalyst A similar experiment to Example 4 was performed using a 5 wt. % vanadium oxide-coated glass bead catalyst. This catalyst was used in a reaction with a set temperature 525° C. After about 50 hours on stream, coking of the reactor was observed.

The reaction conditions are set forth below in Table 14. Table 15 reports the temperature at various points in the reactor during the reaction. The "Bottom Temperature" below is the temperature at the feed nozzle. Table 16 reports the product profile of the reaction product.

TABLE 14

| Run | Time On Stream (hours) | $N_2$ Flow Rate (ml/min) | Water Flow Rate (ml/min) | Feed Flow Rate (ml/min) | Water Vapor Flow Rate (ml/min) | Residence Time (s) | Mass Collected (g) | % Recovery |
|---|---|---|---|---|---|---|---|---|
| R73-22-27 | 27 | 4652.79 | 0.00 | 1.65 | 0.00 | 0.99 | 16.37 | 95.64 |
| R73-22-50 | 50 | 4653.22 | 0.86 | 0.79 | 0.86 | 0.96 | 1.87 | 23.70 |

TABLE 15

| Run | Time On Stream (hours) | Top Temperature (° C.) | Upper Middle Temperature (° C.) | Middle Temperature (° C.) | Bottom Temperature (° C.) |
|---|---|---|---|---|---|
| R73-22-27 | 27 | 545.83 | 548.66 | 628.23 | 97.73 |
| R73-22-50 | 50 | 545.83 | 541.59 | 628.23 | 97.73 |

TABLE 16

| Run | Time on Stream (hours) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|
| R73-22-27 | 27 | 0.11 | 68.70 | 9.39 | 3.43 | 9.30 | 2.90 | 1.41 | 4.78 |
| R73-22-50 | 50 | 0.00 | 15.92 | 2.99 | 0.62 | 2.47 | 0.82 | 3.81 | 10.40 |

Example 8: Pyrolysis of Dextrose Utilizing a Molybdenum-Coated Quartz Sand Catalyst A similar experiment to Example 4 was performed using a cracking media that was approximately 5 wt. % molybdenum-coated quartz sand catalyst and 95 wt. % untreated quartz sand. The reaction was conducted at a set temperature of 525° C. The reaction conditions are set forth below in Tables 17 and 18. The "Bottom Temperature" reported below is the temperature at the feed nozzle. Table 19 reports the results of the experiment.

After 3 hours on stream the reaction was stopped, and the reactor was inspected. Coking was observed and a solid mass had formed in the reactor.

TABLE 17

| Run | Time On Stream (hours) | $N_2$ Flow Rate (ml/min) | Feed Flow Rate (ml/min) | Residence Time (s) | Mass Collected (g) | % Recovery |
|---|---|---|---|---|---|---|
| R74-22-3 | 3 | 4992.48 | 1.60 | 0.94 | 13.46 | 81.18 |

TABLE 18

| Run | Time On Stream (hours) | Top Temperature (° C.) | Upper Middle Temperature (° C.) | Middle Temperature (° C.) | Bottom Temperature (° C.) |
|---|---|---|---|---|---|
| R74-22-3 | 3 | 535.69 | 536.08 | 593.37 | 73.45 |

TABLE 19

| Run | Time on Stream (hours) | Glucose (wt. %) | Glycolaldehyde (wt. %) | Formaldehyde (wt. %) | Glyoxal (wt. %) | Pyruvaldehyde (wt. %) | Acetol (wt. %) | Carbon Dioxide (wt. %) | Carbon Monoxide (wt. %) |
|---|---|---|---|---|---|---|---|---|---|
| R74-22-3 | 3 | 0.00 | 8.72 | 5.50 | 1.82 | 0.00 | 0.00 | 1.58 | 8.07 |

Example 9: Pyrolysis of Dextrose Utilizing a Titania-Coated Glass Bead Catalyst

A titania oxide-coated glass bead was prepared in accordance with the procedure of Example 1 and an experiment for the pyrolysis of dextrose with this catalyst was tested in accordance with the procedure of Example 4. The reaction product profile is reported below in Table 20.

Prior to conducting the reaction, the entire reactor body and all gas handling lines were properly cleaned. The reactor failed to run for longer than 30 hours before completely sealing off. Upon investigation, a solid mass had formed in the reactor and the gas handling lines had become sealed with a mixture of char and pyrolysis oil. It was hypothesized that after injection, the feed reacted with the glass beads to form a solid mass and elevated amounts of char. This buildup ultimately caused the reactor to shut down to a pressure buildup.

TABLE 20

| Run | Time On Stream (hours) | Glycol-aldehyde (wt. %) | Form-aldehyde (wt. %) | Glyoxal (wt. %) | Pyruv-aldehyde (wt. %) | Acetol (wt. %) | Carbon Dioxide (wt. %) | Carbon Monoxide (wt. %) |
|---|---|---|---|---|---|---|---|---|
| R71-22-22 | 22 | 71.35% | 8.36% | 8.36% | 9.43% | 1.97% | 1.48% | 3.67% |

Example 10: Preparation of ZIF-4 Catalyst

In a flask, 3.641 g of zinc nitrate hexahydrate and 2.40 g imidazole were combined. 240 ml of N,N-dimethylformamide was added and a reflux condenser was affixed to the outlet of the flask. The contents were heated at approximately 130° C. for a period of 48 hours with low-speed stirring utilizing a stir bar. The solids were readily dissolved, forming a clear solution with the application of heat. As the reaction progressed, a white precipitant was observed. The precipitant was subsequently rinsed with water and dried under vacuum to form the ZIF-4 catalyst.

Example 11: Testing of Various Catalyst for Conversion of Glycolaldehyde

Various catalysts were tested for the ability to condense at least a portion of the glycolaldehyde to produce threose, erythrose, and/or erythrulose. In this experiment, a calcium-form ion exchange resin (PCR560 Ca), Linde Type-A zeolite, a commercial zeolite (Sigma Aldrich product number #96096), commercial zeolite (Sigma Aldrich product number #96096) that had been acid-treated with hydrochloric acid, calcium hydroxide, and a ZIF-4 catalyst of Example 10 were tested.

Approximately 40 mg of each catalyst was added to 2 ml of a diluted pyrolysis product (containing approximately 5.8 wt. % glycolaldehyde). For each catalyst, was evaluated at 1 and 2 hours. The samples were analyzed using HPLC in order to determine the amount of glycolaldehyde consumed, based on a mole percentage of the starting pyrolysis product material, and to evaluate the spectra for desirable products. The results are set forth below in Table 21.

TABLE 21

| Catalyst | Time (hr) | Glycolaldehyde Consumed (%) | Comments |
|---|---|---|---|
| Calcium-form ion exchange resin (PCR560 Ca) | 1<br>2 | 10<br>7 | No observable change in spectra and/or formation of product peaks |
| Linde Type-A zeolite | 1<br>2 | 20<br>24 | No observable change in spectra and/or formation of product peaks |
| Commercial zeolite from Sigma Aldrich | 1<br>2 | 17<br>21 | No observable change in spectra and/or formation of product peaks |
| Commercial zeolite from Sigma Aldrich that had been acid-treated with hydrochloric acid | 1<br>2 | 9<br>94 | — |
| Calcium hydroxide | 1<br>2 | 92<br>92 | No meaningful formation of product peaks observed |
| ZIF-4 catalyst of example 1 | 1<br>2 | 26<br>42 | Product peaks observed |

Screening of these compounds indicated that the ZIF-4 catalyst outperformed the other catalysts at both the 1 and 2-hour time points in terms of formation of desirable products.

To verify the results, additional experiments were run utilizing a ZIF-4 catalyst. The results for the ZIF-4 catalyst are set forth below in Table 22. The results are normalized for threose and erythrulose only.

TABLE 22

| Time (hr) | Threose/Erythrose (wt. %) | Erythrulose (wt. %) |
|---|---|---|
| 4 - A | 38.02% | 61.98% |
| 4 - B | 39.60% | 60.40% |

Example 12: Testing of a ZIF-4 Catalyst for Conversion of Glycolaldehyde

The experiment of Example 11 was repeated with a second ZIF-4 catalyst and a 5.4 wt. % glycolaldehyde solution. Sampling and analysis of the reaction mixture was conducted at 2, 4, and 6 hours. Similar threose, erythrose, and erythrulose yields were achieved as compared to those reported in Example 12 for the conversion of a pyrolysis product. The results are set forth below in Table 23.

TABLE 23

| Time (hr) | Threose/ Erythrose (wt. %) | Erythrulose (wt. %) | Glycolaldehyde (wt. %) | Total $C_4$ sugars and ketose sugars (wt. %) |
|---|---|---|---|---|
| 2 | 33.22% | 19.53% | 37.03% | 52.74% |
| 4 | 39.98% | 52.19% | 8.55% | 92.17% |
| 6 | 39.24% | 55.64% | 4.22% | 94.88% |

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above processes without departing from the scope of the invention, it is intended that all matter contained in the above description shall be interpreted as illustrative and not in a limiting sense.

What is claimed is:

1. A process for preparing a C4 aldose and/or ketone thereof, the process comprising:

contacting a feed composition comprising glycolaldehyde with a catalyst comprising an imidazolate framework in a reaction zone to condense at least a portion of the glycolaldehyde to the $C_4$ aldose and/or ketone thereof.

2. A process for preparing a C4 aldose and/or ketone thereof, the process comprising:

feeding a feed composition comprising a carbohydrate having at least four carbon atoms to a pyrolysis reaction zone;

pyrolyzing the carbohydrate in the presence of water and a catalyst in the pyrolysis reaction zone to form a reaction product comprising glycolaldehyde, wherein the catalyst comprises a metal oxide on a catalyst support and at least one of the following conditions is satisfied:

(a) the pyrolysis reaction zone is heated to a temperature of 400° C. or greater;

(b) the catalyst support has a BET specific surface area that is 500 $m^2/g$ or less, 250 $m^2/g$ or less, 100 $m^2/g$ or less, 50 $m^2/g$ or less, 25 $m^2/g$ or less, 10 $m^2/g$ or less, 5 $m^2/g$ or less, or 1 $m^2/g$ or less;

(c) the catalyst support comprises a glass, ceramic, or refractory material;

(d) the pyrolysis reaction zone further comprises a reaction zone media that is different than the catalyst; and/or (e) the yield of glycolaldehyde is 70% or greater, 75% or greater, or 80% or greater; and contacting the reaction product comprising the glycolaldehyde with an imidazolate framework in a reaction zone to condense at least a portion of the glycolaldehyde to the C4 aldose and/or ketone thereof.

3. The process of claim 1, wherein the feed composition comprises a glycolaldehyde concentration of 1 wt. % or greater, 5 wt. % or greater, 10 wt. % or greater, 20 wt. % or greater, 30 wt. % or greater, 40 wt. % or greater, 50 wt. % or greater, 60 wt. % or greater, or 70 wt. % or greater.

4. The process of claim 1 or 2, wherein the feed composition further comprises at least one compound selected from the group consisting of pyruvaldehyde, formaldehyde, acetol, glyoxal, and combinations thereof.

5. The process of claim 4, wherein the feed composition further comprises water.

6. The process of claim 1 or 2, wherein the C4 aldose and/or ketone thereof comprises at least one compound selected from the group consisting of erythrose, threose, erythrulose, and combinations thereof.

7. The process of claim 1, wherein the imidazolate framework comprises one or more metal and/or metalloid.

8. The process of claim 7, wherein the imidazolate framework comprises one or more metal and/or metalloid selected from the group consisting of zinc, cobalt, copper, iron, lithium, boron, and combinations thereof.

9. The process of claim 8, wherein the imidazolate framework is selected from the group consisting of ZIF-4, ZIF-8, ZIF-14, BIF-2Li, BIF-2Cu, BIF-5, and combinations thereof.

10. The process of claim 9, wherein the imidazolate framework comprises a ZIF-4.

11. The process of any one of claims 8-10, wherein the imidazolate framework and/or the catalyst is free or essentially free of tin, zirconia, and/or silica.

12. The process of claim 1 or 2, wherein the condensing reaction is conducted at a temperature of 100° C. or less, 95° C. or less, 90° C. or less.

13. The process of claim 1 or 2, wherein the condensing reaction is conducted at a temperature of 0° C. or greater, 25° C. or greater, 50° C. or greater, or 80° C. or greater.

14. The process of claim 1 or 2, wherein the condensing reaction is conducted at a pH of 7 or less, 6 or less, or 5 or less.

15. The process of claim 14, wherein the condensing reaction is conducted free or essentially free of added base.

16. The process of claim 1 or 2, wherein the feed composition and/or reaction zone for the condensing reaction is free or essentially free of an alcohol solvent.

17. The process of claim 1 or 2, wherein the feed composition and/or reaction zone for the condensing reaction is free or essentially free of an organic solvent.

* * * * *